United States Patent [19]

Hänssle

[11] 4,315,867
[45] Feb. 16, 1982

[54] SECONDARY AND TERTIARY 2-CARBOXYETHYL- AND CARBOXYMETHYLPHOSPHINES AND THE SALTS THEREOF, AS WELL AS THEIR PREPARATION AND USE

[75] Inventor: Peter Hänssle, Haltern, Fed. Rep. of Germany

[73] Assignee: Chemische Werke Huels, Aktiengesellschaft, Marl, Fed. Rep. of Germany

[21] Appl. No.: 112,754

[22] Filed: Jan. 17, 1980

[30] Foreign Application Priority Data

Jan. 2, 1979 [DE] Fed. Rep. of Germany ....... 2902202

[51] Int. Cl.³ .............................................. C07F 15/00
[52] U.S. Cl. ........................... 260/439 R; 252/431 P; 260/440; 260/446; 260/447; 562/512; 562/606; 585/514; 568/8; 568/14
[58] Field of Search .................................... 260/439 R

[56] References Cited

U.S. PATENT DOCUMENTS

| | | | |
|---|---|---|---|
| 3,635,937 | 1/1972 | Bauer et al. ................. | 252/431 P X |
| 3,636,091 | 1/1972 | Mason ............................. | 260/514 R |
| 3,644,563 | 2/1972 | Bauer et al. ................ | 260/683.15 D |
| 3,647,914 | 3/1972 | Glockner et al. ......... | 260/683.15 D |
| 3,647,915 | 3/1972 | Bauer et al. ............... | 260/683.15 D |
| 3,676,523 | 7/1972 | Mason ........................ | 260/683.15 D |
| 3,686,351 | 8/1972 | Mason ........................ | 260/683.15 D |
| 3,737,475 | 6/1973 | Mason ........................ | 260/683.15 D |
| 3,758,558 | 9/1973 | Mason et al. ................... | 260/515 M |
| 3,825,615 | 7/1974 | Lutz ........................... | 260/683.15 D |
| 4,020,121 | 4/1977 | Kister et al. .............. | 260/683.15 D |

FOREIGN PATENT DOCUMENTS 997897 9/1976 Canada .

OTHER PUBLICATIONS

Podlahova, Collect. Czech. Chem. Comm., vol. 43, 3007–3011 (1978).
Yakovenko et al., Translated from Zhurnal Obshchei Khimii vol. 46, No. 2, pp. 278–280 (1976).

*Primary Examiner*—Helen M. S. Sneed
*Attorney, Agent, or Firm*—Millen & White

[57] ABSTRACT

Secondary and tertiary 2-carboxyethyl or carboxymethylphosphines or a salt thereof, of the formula

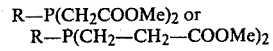

R—P(CH$_2$COOMe)$_2$ or
R—P(CH$_2$—CH$_2$—COOMe)$_2$ wherein
Me is hydrogen, an alkali metal or NR'$_4$ wherein R' is hydrogen, C$_{1-10}$ alkyl or C$_{6-14}$ aryl, and
R is hydrogen or a saturated or unsaturated, aliphatic or cycloaliphatic group of 1–20 carbon atoms and, for the 2-carboxyethylphosphines, also C$_{6-14}$ aryl, are useful as components in catalysts for ethylene oligomerization.

4 Claims, No Drawings

SECONDARY AND TERTIARY 2-CARBOXYETHYL- AND CARBOXYMETHYLPHOSPHINES AND THE SALTS THEREOF, AS WELL AS THEIR PREPARATION AND USE

BACKGROUND OF THE INVENTION

Included among the known 2-carboxyethyl- and carboxymethylphosphines and the alkali metal salts thereof are: tris(2-carboxyethyl)phosphine [Journal of General Chemistry of the USSR 46: 275 (1976)[1]] and bis(carboxymethyl)phenylphosphine, as well as the sodium and potassium salts thereof [Collect. Czechslov. Chem. Commun. 43: 57 (1978)[2]].

Such phosphines are used for flameproofing polymers (1) and for complexing metal ions (2). According to (1), tris(2-carboxyethyl)phosphine is obtained by heating the corresponding nitrile to 90°–95° C. with a strongly acidic ion exchanger, vacuum-filtering the ion exchanger and evaporating the resultant aqueous solution. According to (2), bis(carboxymethyl)phenylphosphine is produced by reacting the Reformatsky reagent $BrZnCH_2COOC_2H_5$ with phenyldichlorophosphine, saponifying the thus-formed ester $C_6H_5P(CH_2COOC_2H_5)_2$ with sodium hydroxide solution and treating the resultant sodium salt with 10% sulfuric acid. In both cases, the phosphinocarboxylic acid is only produced in moderate yields. Additionally, the mentioned synthesis for the production of bis(carboxymethyl)phenylphosphine is a multistage one and, consequently, is expensive.

These disadvantages are becoming increasingly significant since carboxyalkyl phosphines have gained increasing industrial importance. For example, it is known from DAS's [German Published Applications] 1,955,828 and 2,022,184 to utilize such compounds as ligands for transition metal catalysts in the hydroformulation of olefins. It is also known from DOS's [German Unexamined Laid-Open Applications] 2,053,758; 2,054,009; 2,054,083; 2,159,370; 2,234,734; 2,264,088; 2,341,472; 2,445,362; and 2,656,383 to employ tertiary organophosphorus compounds of the formula $R''_2P(CH_2)_n$-COOM wherein n=1 or 2; M=H or an alkali metal; and $R''$=a monovalent organic residue of 1-20 carbon atoms, as nickel ligands in ethylene oligomerization.

SUMMARY OF THE INVENTION

Accordingly, it is an object of the present invention to provide novel secondary and tertiary 2-carboxyethyl- and carboxymethylphosphines and the salts thereof, which can be prepared in high yields by a simple and economical process and which can be utilized advantageously, e.g., in ethylene oligomerization as compared to known carboxyalkyl phosphines.

Upon further study of the specification and appended claims, further objects and advantages of this invention will become apparent to those skilled in the art.

These objects have been attained by this invention by providing novel secondary and tertiary 2-carboxyethyl- and carboxymethylphosphines as well as the salts thereof, of the formulae $R-P(CH_2COOMe)_2$     (I)

or $R-P(CH_2-CH_2-COOMe)_2$     (II)

wherein
Me is hydrogen, an alkali metal or $NR'_4$, $R'$ being hydrogen and/or an alkyl or aryl residue, and
R is hydrogen; a straight-chain, branched or cyclic saturated or unsaturated aliphatic residue of 1–20 carbon atoms; or, for Formula II, an optionally substituted aryl residue of 6–14 carbon atoms.

In other aspects of this invention, these objects have been attained by providing a process for the preparation of these compounds and the use thereof as a catalyst component in the oligomerization of ethylene via a nickel catalyst.

DETAILED DISCUSSION

The residue R in the bis(carboxymethyl)phosphines and bis(2-carboxyethyl)phosphines of Formulae I and II is suitably hydrogen or a monovalent organic $C_{1-20}$ residue, preferably $C_{1-10}$ residue, such as, for example, a saturated or unsaturated, aliphatic or cycloaliphatic residue. Specific examples of suitable residues R include alkyl residues, such as methyl, ethyl, propyl, isobutyl, lauryl, stearyl, cyclopentyl, or cyclohexyl; alkenyl residues, such as butenyl, hexenyl or cyclohexenyl and alkynyl residues such as propynyl or butynyl. Additionally, in the bis(2-carboxyethyl)phosphines of Formula II, R can be an optionally substituted aryl residue of 6–14 carbon atoms in the aromatic system. Specific examples include phenyl, tolyl or xylyl. Equivalent aryl groups are the same R aryl groups substituted by $C_{1-10}$ alkyl, for example ethyl, butyl, decyl, 2-ethylhexyl and cyclohexyl.

Suitable $R'$ groups include, e.g., $C_{1-10}$ alkyl and $C_{6-14}$ aryl.

Typical compounds of this invention include bis(carboxymethyl)phosphine, bis(carboxymethyl)methylphosphine, bis(carboxymethyl)butylphosphine, bis(carboxymethyl)cyclohexylphosphine, bis(carboxymethyl)butenyl-4-phosphine, bis(carboxymethyl)hexenyl-6-phosphine, bis(carboxymethyl)cyclohexenylphosphine, bis(2-carboxyethyl)phosphine, bis(2-carboxyethyl)methylphosphine, bis(2-carboxyethyl)butylphosphine, bis(2-carboxyethyl)cyclohexylphosphine, bis(2-carboxyethyl)butenyl-4-phosphine, bis(2-carboxyethyl)hexenyl-6-phosphine, bis(2-carboxyethyl)cyclohexenylphosphine, bis(2-carboxyethyl)phenylphosphine, bis(2-carboxyethyl)tolylphosphine, and, respectively, the ammonium or alkali metal salts, preferably the sodium and potassium salts thereof. For the salts, it is not necessary for all carboxy groups of a molecule to be in the salt form.

The secondary and tertiary 2-carboxyethyl- and carboxymethylphosphines of this invention can be prepared by a special process of this invention. The corresponding cyanoalkyl phosphines are first saponified with an aqueous-alcoholic alkali metal hydroxide solution. Thereafter, the aqueous solution of the acid salts is treated with an acidic ion exchanger and the free acids are optionally neutralized with an alkali metal hydroxide or ammonia or an amine. This process is the subject of copending application Ser. No. 112,687, filed on even date, whose disclosure is incorporated by reference herein.

The cyano alkyl phosphines used as the starting compounds may be produced by known processes. [See, e.g., Journal of the Chemical Society, London (1952):

4453; Journal of the American Chemical Society 81: 1103 and 4803 (1959); and Acta Chemical Scandinaciva B 30: 799 (1976)].

Suitable alcohols for use in the aqueous-alcoholic alkali metal hydroxide solutions are the water-miscible and low-boiling (<100° C.) alcohols, preferably methanol and ethanol. Alkali metal hydroxides suitable for this purpose are preferably sodium and potassium hydroxide.

Suitable ion exchangers include all commercial cation exchangers readily convertible into the acid form, preferably strongly acidic cation exchangers which contain $SO_3$-groups [see, e.g., Jander-Wendt, "Lehrbuch der analyt. und. praep. anorg. Chemie" [Textbook of Analytical and Preparative Inorganic Chemistry], 3rd Edition (1959): 44–46[3], whose disclosure is incorporated by reference herein]. These ion exchangers should have an absorption capacity of 1–4 meq./ml, especially about 2 meq./ml of resin. To convert the cation exchangers into the $H^{\oplus}$ form (acid form), 2 N hydrochloric acid is preferably utilized. Thereafter, the reaction mixture is washed free of chloride and acid with distilled water. If the cation exchangers cannot be obtained at sufficient purity, care must be taken, as is conventional, that the impurities are simultaneously removed during this procedure (for example, $Fe^{3+}$ ions). See, for example[3].

In detail, the secondary and tertiary 2-carboxyethyl- and carboxymethylphosphines of this invention, as well as the salts thereof, can be prepared as described hereinbelow. 15–25 g of the cyano alkyl phosphine is dissolved in 20–50 ml of an alcohol-water mixture (general volume ratio of alcohol:water = 1:1 to 10:1, preferably about 4:1), combined with the equivalent amount of alkali metal hydroxide, and the mixture is refluxed (general reaction temperature is 65°–100° C.) until the evolution of ammonia has ceased, e.g., 80–110 hours. The reaction mixture is then concentrated to dryness. The residue is dissolved in distilled water and extracted twice with diethyl ether, for example, to remove unreacted cyano alkyl phosphine. The aqueous solution is optionally filtered, and the filtrate is again evaporated to dryness. At this stage, the reaction has prepared the alkali metal salt of the corresponding phosphinocarboxylic acid.

If it is intended to synthesize the free acid instead of the alkali metal salt, the last evaporation phase can be omitted. The optionally filtered aqueous salt solution is then immediately treated (e.g., at 20°–30° C.) with at least the equivalent quantity, e.g., 0,25–1 equivalents, of the strongly acidic cation exchanger in the $H^{\oplus}$ form. Preferably the salt solution is allowed to pass through a column, the dripping speed being adjusted so that a flawless ion exchange is ensured. The water of the acid solution is withdrawn, and the desired carboxy alkyl phosphine remains behind. Details of the acid exchange reaction may be determined by fully conventional considerations, as described, for example, in [3] whose disclosure is incorporated by reference herein.

This carboxy alkyl phosphine can optionally be converted into an alkali metal salt or an ammonium salt by conventional reaction with an alkali metal hydroxide, with ammonia or with an amine. Suitable amines include, for example, triethylamine, dibutylamine, butylamine, diphenylamine, tridecylamine and the like. Especially preferred are secondary amines due to their strong basicity.

Considering the nature and results of conventional methods for the preparation of carboxy alkyl phosphines, it is surprising that the 2-carboxyethyl- and carboxymethylphosphines, as well as the salts thereof, of this invention can be produced in a pure form and in high yields by the process of this invention.

The novel 2-carboxyethyl- and carboxymethylphosphines prepared according to the claimed process, as well as the salts thereof, are used primarily as catalyst components in the oligomerization of ethylene by a nickel catalyst. However, it is also possible to utilize these compounds, for example, for flameproofing polymers and or complexing metal ions or metal atoms.

Processes are known for ethylene oligomerization wherein ethylene is treated in the liquid phase with a nickel complex. The nickel complex contains a nickel atom chelated with a bidentate ligand. Suitable bidentate ligands contain a tertiary organophosphorus component and a single additional functional group, containing active hydrogen, on a carbon atom. This carbon atom is linked either directly to the phosphorus or is separated therefrom at most by one carbon atom. A preferred functional group is the carboxy or alkali metal carboxylate group (DOS's 2,053,758; 2,054,009; 2,054,083; 2,159,370; 2,234,734; 2,264,088; 2,341,472; 2,445,362; and 2,656,383.

Among the compounds employed are the o-dihydrocarbylphosphinobenzoid acids and the alkali metal salts thereof, such as, for example, o-diphenylphosphinobenzoic acid. Other preferred tertiary organophosphorus compounds are dihydrocarbylphosphinoacetic) and -propionic acids and the alkali metal salts thereof. These can be represented by the formula $R_2P-(CH_2)_n-COOM$ wherein $n=1$ or 2 and $M=H$ or an alkali metal. R is a monovalent organic $C_{1-20}$ residue which can additionally comprise hetero atoms in the form of functional groups which, however, must not contain active hydrogen atoms.

Suitable nickel components include compounds of zerovalent nickel, e.g., bis[cyclooctadiene-(1,5)]nickel(0), or bivalent nickel salts (as the starting compound) for example, $NiCl_2.6H_2O$, which are then reduced in the presence of the abovementioned tertiary phosphines and in the presence of ethylene with a boron hydride reagent in polar organic solvents such as, for example, ethylene glycol or 1,4-butanediol. (See below.)

The olefin mixtures obtained with such prior art catalyst systems after approximately three hours of a discontinuous ethylene oligomerization experiment in 1,4-butanediol at 70° C. and under an ethylene pressure of 50 bar has an n-α-olefin proportion, determined by infrared spectroscopy, of about 96% by weight. The extent of isomerization is 2–3% by weight, measured by the butene-2 content in the thus-produced butene, determined by gas chromatography.

In contradistinction, when using the 2-carboxyethyl- and carboxymethylphosphines and the salts thereof according to this invention, olefin mixtures are obtained having an n-α-olefin proportion of 98% by weight and a degree of isomerization of 0.6–1.0% by weight.

Furthermore, the nickel catalyst can be complexed with a great variety of different organic ligands, provided that the nickel catalyst contains the carboxyalkyl phosphines of this invention.

In general, the nickel atom is linked as in a complex and/or chemically to the phosphorus-containing, chelate-forming ligand, as well as to a number of organic complex-forming ligands sufficient that the desired coordination number of the nickel atom, being preferably 4, is attained. Additional organic complex-forming ligands include any desired ligands different from the aforementioned required ligands, which latter contain phosphorus and several carboxy or carboxylate groups, these additional ligands being complexed to the nickel atom to attain the coordination number of the nickel atom. In general, suitable ligands for this purpose are organic ligands, such as a phosphine, phosphite, phosphino alkylene, arsine, stibine or bismuthine. Preferred complexing ligands are olefinically unsaturated compounds of 2-20 carbon atoms, containing up to four olefinically unsaturated linkages and up to 3 carbocyclic rings. An especially preferred class of olefinically unsaturated compounds are the $C_{2-12}$ olefins of the formula

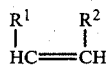

wherein $R^1$ and $R^2$ are alike or different and are hydrogen or alkyl, cycloalkyl, alkenyl, cycloalkenyl, aralkyl, aryl or alkaryl of up to 8 carbon atoms each, and wherein $R^1$ and $R^2$ together can also form a bivalent aliphatic $C_{2-10}$ group having up to 3 additional olefinically unsaturated linkages as the only unsaturated C-C bonds. Specific examples of olefins of this formula include ethylene, propylene, butene-2, 1-pentene, 1-hexene, 1-octene, 1-decene, butadiene, isoprene, 1,3,5-octatriene, 1,3,7-octatriene, cyclopentene, cycloheptene, cyclopentadiene, 1,3-cyclohexadiene, 1,5-cyclooctadiene (COD), cyclooctatriene and cyclododecatriene.

Specific examples of the nickel chelates include diethylenebis(carboxymethyl)butylphosphine nickel, butadienebis(2-carboxyethyl)phosphine nickel, cyclooctadienebis(2-carboxyethyl)phenylphosphine nickel and cyclooctadienebis(2-carboxyethyl)butylphosphine nickel.

The nickel chelate catalysts can be prepared according to a great variety of methods. In accordance with a preferred prior art method, they can be obtained by treating an olefin-nickel compound with the carboxy alkyl phosphines of this invention or the salts thereof. A special class of olefin-nickel compounds are those of the formula

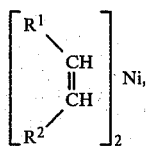

wherein $R^1$ and $R^2$ are as defined above. Specific examples include bis(cyclooctadiene)nickel(0), bis(cyclooctatetraene)nickel(0) and bis(1,3,7-octatriene)nickel(0).

Another class of olefin-nickel compounds suitable as preliminary products are π-allylnickel compounds wherein a nickel-containing agent segment is linked to a π-allyl segment such that there is a spatial shift of the electron component contributed by the π-allyl segment between the three linked carbon atoms. Preferred π-allyl portions comprise 3-12 carbon atoms and are otherwise free of aliphatic unsaturation, except when the π-allyl portion represents part of a closed ring system.

Suitable π-allylnickel compounds include π-allylnickel chloride, π-allylnickel bromide, π-crotylnickel chloride, π-methylallylnickel chloride, π-ethylallylnickel iodide, π-cyclopentenylnickel bromide, π-cyclooctenylnickel chloride, π-cyclooctadienylnickel chloride, π-cinnamylnickel bromide, π-phenylallylnickel chloride, π-cyclohexenylnickel bromide, π-cyclododecenylnickel fluoride and π-cyclododecatrienylnickel chloride. Other suitable π-allylnickel compounds include π-allylnickel acetate, π-methylallylnickel octoate, π-allylnickel methylate, π-allylnickel ethylate and π-methylallylnickel propionate.

Also suitable as preliminary products are bis(π-allyl)nickel compounds. Specific examples include bis(π-allyl)nickel, bis(π-methylallyl)nickel, bis(π-cinnamyl)nickel, bis(π-octadienyl)nickel, bis(π-cyclohexenyl)nickel, π-allyl-π-methylallyl-nickel, bis(π-cyclooctatrienyl)nickel and bis(π-crotyl)nickel.

The olefin-nickel catalyst component and the phosphorus-containing ligand catalyst components are generally utilized in a molar ratio of 0.5:1 to 5:1, preferably about 1:1. The nickel chelate catalyst is suitably preformed by treating the preliminary catalyst products in an inert diluent, for example, in those diluents which can also be used in the subsequent oligomerization. According to a modified method, the preliminary catalyst product components are brought into contact with one another at the beginning of the oligomerization process in the presence of the ethylene serving as the starting material. In either of the two methods, the preliminary catalyst product components are advantageously brought into contact at temperatures of 25°-100° C.

In addition to nickel (0) complexes, it is also possible to start with bivalent nickel salts which are reduced in the presence of ethylene and the secondary or tertiary carboxyalkyl phosphines of this invention as well as the salts thereof, with a boron hydride reagent. In this case, no expensive nickel compounds—which are unstable oxidatively and thermally—are required, such as, for example bis[cyclooctadiene-(1,5)]nickel (0). In general, any simple bivalent nickel salt can be used for producing the catalyst, provided that the nickel salt dissolves sufficiently in the reaction medium. The designation "simple bivalent" nickel salt means a nickel salt wherein the metal has an oxidation number of 2 and is bound via ionic or electrovalent linkages to two monovalent anionic groups (e.g., halogenide groups) or to a bivalent anionic group (e.g., a carbonate group), rather than being bound in a complex or coordinative manner to any additional molecules or ions. Nickel salts containing water of crystallization in addition to one or two anionic groups in bound form, however, are designated as simple bivalent nickel salts herein. In most cases, a simple bivalent nickel salt having a solubility in the reaction diluent or solvent used for the catalyst preparation of at least 0.001 mole per liter (0.001 molar) is suitable as the starting material for the nickel catalyst. A nickel salt having a solubility of at least 0.002 mole/liter (0.002 molar) is preferably utilized, and most preferred is a nickel salt having a solubility of at least 0.005 mole/liter (0.005 molar). Inorganic as well as organic bivalent nickel salts are suitable as the simple bivalent nickel salts. Suitable inorganic nickel salts include nickel halides, e.g., nickel chloride, nickel bromide and nickel iodide, nickel carbonate, and nickel nitrate. Suitable organic nickel salts include nickel salts of carboxylic acids, such as the nickel salts of fatty acids of up to 10 carbon atoms and preferably of up to 6 carbon atoms, e.g., nickel formate, nickel acetate, nickel propionate, nickel hexanoate, nickel oxalate, nickel benzoate and nickel naphthenate. Other suitable organic salts are nickel benzenesulfonate, nickel citrate, nickel dimethylglyoxime and nickel acetylacetonate. Nickel halides, especially nickel chloride, and nickel alocholates are preferably employed, inter alia because of their low price and their solubility in polar organic solvents.

As in the case of the zerovalent nickel compounds, a molar ratio of nickel salt to the phosphorus-containing ligands of 0.5:1 to 5:1, preferably about 1:1, is generally employed in the preparation of the catalyst.

Suitable boron hydride reducing agents include: alkali metal boron hydrides, such as sodium borohydride, potassium borohydride, and lithium borohydride; alkali metal alkoxyboron hydrides, wherein each alkoxy residue contains 1–4 carbon atoms, such as sodium trimethoxyborohydride and potassium tripropoxyborohydride; and tetraalkylammonium boron hydrides, wherein each alkyl residue contains 1–4 carbon atoms, such as tetraethylammonium borohydride. Above all, alkali metal boron hydrides and especially sodium borohydride are utilized since they are readily available commercially. In the preparation of the catalyst, the molar ratio of boron hydride salt to nickel is at least 1:1. There does not seem to be a specific upper limit for the ratio of boron hydride reagent to nickel. For reasons of economy, however, the molar ratio generally will not exceed a value of 15:1. The preferred ratio of boron hydride to nickel salt is ordinarily between 1:1 and 10:1. The best results are obtained with a molar ratio of about 4:1. The catalyst can suitably be prepared by contacting the starting materials for the catalyst, i.e., the nickel salt, the organophosphorus compound and the boron hydride reducing agent, in the presence of ethylene in a polar organic diluent or solvent which is not reduced by the boron hydride reagent, preferably in the polar organic solvent also utilized in the oligomerization process of this invention. In a preferred embodiment, the solvent, the nickel salt and the carboxyalkyl phosphines are contacted in the presence of ethylene prior to admixing the boron hydride reducing agent. To obtain the catalyst of this invention, the presence of ethylene during catalyst preparation is essential. In general, the starting materials for preparing the catalyst are contacted under ethylene pressure of 0.7–100 bar.

Independently of the choice of catalyst components, the catalyst preparation is carried out in a temperature range of 0°–50° C., preferably 10°–30° C. Contact times of about 5 minutes to up to one hour generally lead to satisfactory results. In the oligomerization reaction, ethylene is contacted with the catalyst in the presence of a solvent which is liquid at the reaction temperature. Amounts of solvent of up to about 30 l/mole of ethylene yield satisfactory results. In general, the catalyst concentration (based on nickel) in the solvent is at least 0.001 mole/liter and preferably 0.005–0.05 mole/liter.

Suitable solvents for the use of nickel(0) compounds as well as nickel(II) salts include nonpolar organic solvents, such as aliphatic or aromatic hydrocarbons. However, preferred solvents are polar organic compounds containing oxygen, sulfur, nitrogen or phosphorus in functional groups, such as, hydroxy, alkoxy, aryloxy, carbalkoxy, alkanoyloxy, cyano, amino, alkylamino, dialkylamino, amido, N-alkylamido, N,N-dialkylamido and sulfonyl alkyl groups. Such organic solvents include glycerin triacetate, pentaerythritol tetraacetate, diethylene glycol diacetate, butyl propionate, phenyl acetate, dioxane, tetrahydrofuran, tetrahydropyran, dimethoxyethane, diethylene glycol dimethyl ether, dibutyl ether, anisole, 1,4-dimethoxybenzene, p-methoxytoluene, methanol, trifluoroethanol, trifluoropropanol, sec-butanol, perfluorobutanol, octanol, dodecanol, cyclopentanol, cyclohexanol, glycerin, trimethylene glycol, cresol, p-chlorophenol, m-bromophenol, 2,6-dimethylphenol, p-methoxyphenol, 2,4-dichlorophenol, carbonic acid ethylene, propylene or butylene esters, acetonitrile, propionitrile, butylamine, dibutylamine, trihexylamine, N-methylpyrrolidine, N-methylpiperidine, aniline, N,N-dimethylformamide, N,N-dimethylacetamide, tetramethylenesulfone (sulfolane), dimethyl sulfoxide, trimethyl phosphate, triethyl phosphate, tributyl phosphate, hexamethylphosphoric triamide and the like. Preferably employed solvents are alkanediols of 2–10 carbon atoms, such as ethylene glycol and propylene glycol. Alkanediols of 4–6 carbon atoms, such as 1,4-butanediol and 2,5-hexanediol, are preferably used.

The reason for preferably using polar organic solvents is that the product mixture of the ethylene oligomerization is practically insoluble therein. The use of a polar organic solvent such as, for example, an alkanediol, leads to the formation of a two-phase reaction mixture, i.e., one phase containing the ethylene oligomerization product mixture, namely with the α-olefins, and a second phase containing the nickel catalyst and the solvent. With the formation of this two-phase reaction mixture, the ethylene oligomerization product can be readily separated, and the solvent phase containing the catalyst can be reused for further ethylene oligomerization. As indicated above, the polar organic solvents are furthermore preferred because they are also used in the preparation of the catalyst. Water, which contains a certain proportion of a polar organic solvent, can also be utilized as the diluent or solvent. Mixtures of water and a polar organic solvent generally consist of 40–90% by volume of this solvent and 10–60% by volume of water. Unless indicated otherwise herein, the preparation of the final nickel catalyst of this invention is carried out using fully conventional procedures as disclosed, e.g., in DOS's 20 54 009 and 22 34 734 whose disclosure is incorporated by reference herein.

The specific method according to which the ethylene is contacted with the catalyst during the course of the oligomerization is not critical. According to one embodiment, the catalyst components and the solvent are introduced into an autoclave or a similar pressurized reactor under ethylene or under a protective gas, such as nitrogen or argon; if a protective gas is employed, it is displaced by ethylene and a specific ethylene pressure is set. The reaction mixture is maintained at the reaction temperature and the corresponding pressure under agitation during the desired period of reaction (discontinuous process). In cases wherein a polar organic solvent is employed and a two-phase reaction mixture is formed, ethylene can be continuously introduced into a reaction zone containing the catalyst and the solvent, and the thus-formed mixture of oligomers can be simultaneously withdrawn from the reaction zone (continuous process). Independently of the respective process details, the oligomerization is conducted at the following temperatures and under the following pressures: Suitable reaction temperatures are generally 10°–250° C., preferably 20°–100° C. Suitable pressures are 0.7–350 bar excess pressure, preferably 7–150 bar excess pressure, [gauge].

The oligomerization products are separated from the reaction mixture and obtained by means of customary methods, such as fractional distillation, selective extraction, filtration and adsorption.

The reaction solvent, the catalyst, and any unreacted ethylene can be recycled into the reactor for reuse. If a catalyst is used in the oligomerization consisting of a nickel(II) salt, the carboxy alkyl phosphine of this invention and a boron hydride reagent in a polar organic solvent, the exhausted catalyst, i.e., a catalyst no longer active for ethylene oligomerization, can be regenerated by reaction with additional boron hydride reducing agent and additional nickel(II) salt in the above-indicated molar ratios. No further addition of organophosphorus compounds is required to regenerate the exhausted catalyst.

Unless indicated otherwise herein, the oligomerization reaction is carried out under conventional conditions as is the post reaction work-up, as described, for example, in DOS's 20 54 009 and 22 34 734 whose disclosure is incorporated by reference herein.

The ethylene oligomerized products (essentially n-α-olefins) obtained by the carboxy alkyl phosphines of this invention are present with respect to their C-number distribution according to a geometric distribution scheme. H. Wesslau, Liebigs Ann. 629:198 (1960) derived the following distribution function for the catalytic progression of the α-olefin synthesis:

$$x_p = \frac{\beta}{(1+\beta)^p} p$$

$x_p$ is the mole fraction of the olefins having the composition $CH_2=CH-(C_2H_4)_{p-1}-C_2H_5$ in the reaction mixture (p=number of structural stages of ethylene units; ethylene [p=0] is not included in the count). Parameter $\beta$ indicates the ratio of the velocities of breakdown of the alkyl chain on the nickel to growth (buildup) of the chain, i.e., $\beta=(Va/Vw)$. The equation by H. Wesslau can be converted into a form expressing the distribution more illustratively as weight fraction mp:

$$mp = \frac{\beta^2}{1+2\beta} \cdot \frac{(p+1)}{(1+\beta)} p \quad (p \geq 1; 100 \cdot mp = \% \text{ by weight})$$

To determine parameter $\beta$, it is sufficient to set up, for two n-α-olefins of the mixture which can be readily determined by gas chromatography, the proportion of the relative weight quantity (in grams or % by weight) to be expected according to the following equation, and to eliminate $\beta$ therefrom (Dissertation: R. Streck, RWTH Aachen, 1961):

$$m_{rel}=(p+1)\cdot(1+\beta)^{-p}$$

for example:

$$\frac{\% \text{ 1-hexene}}{\% \text{ 1-octene}} = \frac{3}{4} \cdot \frac{(1+\beta)^{-2}}{(1+\beta)^{-3}} = \frac{3}{4}(1+\beta)$$

$$\beta = \frac{4 \cdot \% \text{ 1-hexene}}{3 \cdot \% \text{ 1-octene}} - 1$$

or $$\frac{\% \text{ 1-hexene}}{\% \text{ 1-decene}} = \frac{3}{5} \cdot \frac{(1+\beta)^{-2}}{(1+\beta)^{-4}} = \frac{3}{5}(1+\beta)^2$$

$$\beta = \sqrt{\frac{5 \cdot \% \text{ 1-hexene}}{3 \cdot \% \text{ 1-decene}}} - 1$$

Ethylene oligomerized products, especially those with 12-20 carbon atoms, are valuable starting materials for preparing detergents, such as α-olefin sulfonates, alcohol oxyethylates and amine oxides. The lower olefins can be processed, for example, to obtain synthetic lubricating oils or plasticizer alcohols; the higher olefins are utilized as waxes, inter alia.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any whatsoever. In the following examples, all temperatures are set forth uncorrected in degrees Celsius; unless otherwise indicated, all parts and percentages are by weight.

The analytical characteristic data were determined according to conventional methods (gas chromatography, infrared spectroscopy and $H^1$ and $C^{13}$ nuclear resonance spectroscopy).

EXAMPLE 1

In a 250-milliliter three-necked flask, 21.6 g (0.1 mole) of bis(2-cyanoethyl)phenylphosphine is combined with a solution of 11.2 g of KOH (0.2 mole) in 21 ml of methanol and 5 ml of water. The reaction mixture is maintained under reflux for about 90 hours until the evolution of ammonia has ceased.

The reaction mixture is evaporated to dryness on a forced circulation evaporator and the residue is dissolved in 100 ml of distilled water and extracted twice with respectively 100 ml of ether. The aqueous phase is completely evaporated, thus yielding 28.7 g, corresponding to 87% of theory, of $C_6H_5$-$P(CH_2CH_2COOK)_2$ as a white powder.

IR (KBr): 690 and 735 cm$^{-1}$ (CH-wagging for 5 neighboring H atoms), 1425 cm$^{-1}$ (P-phenyl), 1580 cm$^{-1}$ ($\nu_{COO}\ominus$).

$H^1$-NMR (D$_2$O): area ratio of aromatic protons (at 2.5τ) to aliphatic protons (at 7.8τ)=5:8.

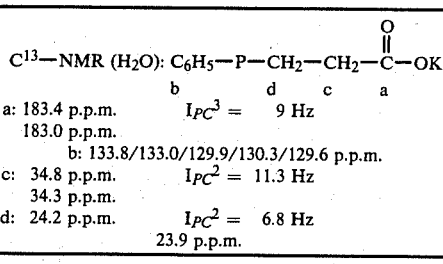

$C^{13}$—NMR (H$_2$O): $C_6H_5$—P—CH$_2$—CH$_2$—$\overset{\overset{O}{\|}}{C}$—OK
                                  b         d         c      a a: 183.4 p.p.m.    $I_{PC}^3 = 9$ Hz
   183.0 p.p.m.
b: 133.8/133.0/129.9/130.3/129.6 p.p.m.
c: 34.8 p.p.m.     $I_{PC}^2 = 11.3$ Hz
   34.3 p.p.m.
d: 24.2 p.p.m.     $I_{PC}^2 = 6.8$ Hz
   23.9 p.p.m.

The potassium salt is dissolved in 100 ml of distilled water and passed over a column packed with 150 ml of strongly acidic ion exchanger ("LEWATIT S 100") in the H$\oplus$ form. Since the acid is only moderately soluble in water, a subsequent washing step with a large volume of 1-1.5 liters of water must be performed. Thereafter the water is withdrawn by means of a forced circulation evaporator. Bis(2-carboxyethyl)phenylphosphine remains as a white powder.

Yield: 22 g=100% of theory, based on the salt.
Melting Point: 202° C.
Analysis: $C_{12}H_{15}O_4P$ (254.2): Calculated: C 56.7 H 5.9 O 25.2 P 12.2%. Found: C 56.4 H 5.6 O 25.9 P 12.1%.

IR (KBr): 690 and 740 cm$^{-1}$ (CH-wagging for 5 neighboring H atoms), 940 cm$^{-1}$ (OH-wagging), 1435 cm$^{-1}$ (P-phenyl) 1720 and 1745 cm$^{-1}$ ($\nu_{COOH}$).

H$^1$-NMR (D$_2$O/NaOH/d-methanol): aromatic protons at 2.35 $\tau$, aliphatic protons at 7.6 $\tau$ (two nestled triplets).

$$C^{13}\text{—NMR (NaOH): } \underset{b}{C_6H_5}\text{—P—}\underset{d}{CH_2}\text{—}\underset{c}{CH_2}\text{—}\underset{a}{\overset{\overset{O}{\|}}{C}}\text{—ONa}$$

a: 180.5 p.p.m.    $I_{PC}{}^3 = 15.8$ Hz
    179.8 p.p.m.
b: 133.3 p.p.m.
    133.1 p.p.m.    for para-C, $I_{PC}{}^{4'} = 4.5$ Hz
    131.0 p.p.m.    for α-C
    130.6 p.p.m.
    130.0 p.p.m.    for m-C, $I_{PC}{}^{3'} = 13.5$ Hz
    129.5 p.p.m.
    128.6 p.p.m.    for o-C, $I_{PC}{}^{2'} = 20$ Hz
c:   29.2 p.p.m.
    29.0 p.p.m    $I_{PC}{}^2 = 4.5$ Hz
d:   27.1 p.p.m.    $I_{PC}{}^1 = 68$ Hz
    24.1 p.p.m.

EXAMPLE 2

In a 250-milliliter three-necked flask, 25 g (0.178 mole) of bis(2-cyanoethyl)phosphine is combined with a solution of 20 g of KOH (0.356 mole) in 38 ml of methanol and 10 ml of water. The reaction mixture is maintained under reflux for 135 hours until the evolution of ammonia has ceased. The mixture is concentrated to dryness in a forced circulation evaporator and the residue is dissolved in 150 ml of distilled water and is extracted twice with respectively 150 ml of ether. The aqueous phase is completely evaporated, thus yielding 38.5 g corresponding to 100% of theory, of H-P(CH$_2$CH$_2$COOK)$_2$ as a white powder.

IR(KBr): 1575 cm$^{-1}$ ($\nu_{COO}{}^{\ominus}$) 2285 cm$^{-1}$ ($\nu_{PH}$).
H$^1$-NMR (D$_2$O): multiplet at 7.64–8.17$\tau$.

$$C^{13}\text{—NMR (methanol): } H\text{—P—}\underset{a}{CH_2}\text{—}\underset{b}{CH_2}\text{—}\underset{c}{\overset{\overset{O}{\|}}{C}}\text{—OK}$$

a: 17–18.2 p.p.m.    $I_{PC}{}^1 = 27.2$ Hz
b: 34.8 p.p.m.
c: 176.7 p.p.m.

The potassium salt is dissolved in 150 ml of warm distilled water and passed over a column packed with 200 ml of strongly acidic ion exchanger ("LEWATIT S 100") in the H$^{\oplus}$ form. The mixture is washed with 3 liters of warm distilled water and then evaporated under vacuum. There remains 20 g (63% of theory) of bis(2-carboxyethyl)phosphine as a viscous, yellow mass.

IR(film): 1670 and 1720 cm$^{-1}$ ($\nu_{COOH}$) 2880 cm$^{-1}$ ($\nu_{PH}$).
H$^1$-NMR (D$_2$O): multiplet at 7.64–8.17$\tau$.

$$C^{13}\text{—NMR (H}_2\text{O): } H\text{—P—}\underset{a}{CH_2}\text{—}\underset{b}{CH_2}\text{—}\underset{c}{\overset{\overset{O}{\|}}{C}}\text{—OH}$$

a: 16.6–16.9 p.p.m.
b: 33.7–35.1 p.p.m.
c: 179.8 p.p.m.

EXAMPLE 3

As indicated in the preceding examples, bis(2-cyanoethyl)-butylphosphine is saponified with KOH to the potassium salt of bis(2-carboxyethyl)butylphosphine, which salt is then converted into the free acid with a strongly acidic ion exchanger, thus obtaining 65% of bis(2-carboxyethyl)butylphosphine as a clear viscous mass.

IR (film): 1710 cm$^{-1}$ ($\nu_{COOH}$), 2935 cm$^{-1}$ ($\nu_{CH_2}$), 2880 and 2970 cm$^{-1}$ ($\nu_{CH_3}$).
H$^1$-NMR (d-methanol):

$$\underset{a}{CH_3}\text{—}\underset{b}{CH_2}\text{—}\underset{b}{CH_2}\text{—}\underset{b}{CH_2}\text{—P(}\underset{c}{CH_2}\text{—CH}_2\text{—COOH)}_2$$

a: 9.05 $\tau$ (triplet, 3 H)
b: 7.9–8.7 $\tau$ (multiplet, 10 H)
c: 7.6 $\tau$ (multiplet, centered, 4 H)

$$C^{13}\text{-NMR (H}_2\text{O): } \underset{a}{CH_3}\text{—}\underset{b}{CH_2}\text{—}\underset{b}{CH_2}\text{—}\underset{b}{CH_2}\text{—P—}\underset{b}{CH_2}\text{—}\underset{c}{CH_2}\text{—COOH}$$

a: 11 p.p.m.
b: 20–30 p.p.m. (8 signals; 3 out of 5 chemical shifts have been split up)
c: 178 p.p.m. $I_{PC}{}^3 = 8$ Hz

EXAMPLE 4

As indicated in the preceding examples, bis(2-cyanoethyl)cyclohexylphosphine is saponified to the potassium salt of bis(2-carboxyethyl)cyclohexylphosphine; this product is then converted into the free acid with strongly acidic ion exchanger. Yield: 46% of bis(2-carboxyethyl)cyclohexylphosphine as a clear, viscous mass.

IR(film): 1720 cm$^{-1}$ ($\nu_{COOH}$), 2860 and 2930 cm$^{-1}$ ($\nu_{CH_2}$).

$$H^1\text{—NMR (D}_2\text{O): } \underset{b}{\langle H \rangle}\text{—P (}\underset{a}{CH_2}\text{—}\underset{b}{CH_2}\text{—COOH)}_2$$

a: 7.5 $\tau$ (multiplet, centered, 4H)
b: 8–8.8 $\tau$ (multiplet, 15H)

$$C^{13}\text{—NMR (H}_2\text{O): } \underset{a\ b}{\langle H \rangle}\text{—P—}\underset{b}{CH_2}\text{—}\underset{c}{CH_2}\text{—COOH}$$

a: 11.4 p.p.m.
    $I_{PC}{}^4 = 50$ Hz
    13.6 p.p.m.
b: 25.3–30.5 p.p.m. 9 signals; 3 out of 6 chemical shifts have been split up)
c: 176.8 p.p.m.
    $I_{PC}{}^3 = 8$ Hz
    177.1 p.p.m.

EXAMPLES 5–8 and COMPARATIVE EXAMPLES A–C 2.5 millimoles of the phosphine ligands listed in Table 1 is dissolved under argon in 500 ml of 1,4-butanediol. Thereafter, 2.5 mmol (=0.7 g) of Ni(COD)$_2$ is suspended in the reaction mixture. This solution or suspension is introduced under argon into a 5-liter steel autoclave. The protective gas is evacuated and, under agitation (1,000 r.p.m.), about 10 bar of ethylene is introduced [ethylene is introduced up to a pressure of about 10 bar].

The content of the autoclave is thereafter heated to 70° C. within about 5 minutes and the ethylene pressure is raised to 50 bar. Under a constant pressure of 50 bar and at an agitating speed of 1,000 r.p.m., the oligomerization is carried out for 165 minutes. The results are compiled in Table 1. The percentage proportion of butene-2 in the total butene was determined by gas chromatography. The n-α-olefin content was determined from the total oligomerized product by IR spectroscopy.

TABLE 1

| Example or Comp. Example | Ligand | Catalyst Activity (g. Olefins/ g. Ni . h) | Isomerization (% Butene-2 in Butene) | β | n-α-Olefin Content (%) |
| --- | --- | --- | --- | --- | --- |
| 5 | $C_6H_5P(CH_2CH_2COOK)_2$ | 450 | 1.0 | 2.8 | 98 |
| 6 | $HP(CH_2CH_2COOH)_2$ | 220 | 0.6 | 3.2 | 98 |
| 7 | $C_4H_9P(CH_2CH_2COOH)_2$ | 300 | 0.9 | 1.7 | 98 |
| 8 | 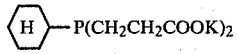 | 100 | 0.7 | 0.5 | 98 |
| A | $(C_6H_5)_2PCH_2COONa$ | 820 | 1.8 | 1.6 | 96 |
| B | $(C_6H_5)_2PCH_2COOH$ | 1570 | 2.5 | 0.7 | 96 |
| C | $(C_6H_5)_2PCH_2CH_2COOH$ | 270 | 3.0 | 1.1 | 96 |

EXAMPLES 9–11

2.5 millimoles of $NiCl_2.6H_2O$ is dissolved in 500 ml of 1,4-butanediol and then, under argon, 2.5 mmol of the ligand $C_6H_5P(CH_2CH_2COOK)_2$ is dissolved therein. The solution is filled under argon into a 5-liter steel autoclave. The protective gas is then evacuated and replaced by 20 bar of ethylene, while agitating for 5 minutes at 1,000 r.p.m. Then, under ethylene (normal pressure), varying amounts of $NaBH_4$ in 2.5 ml of distilled water are introduced into a storage vessel connected with the autoclave. This $NaBH_4$ solution is immediately forced with ethylene into the 5-liter steel autoclave, the ethylene pressure being increased to 35 bar. The catalyst is aged at room temperature and at an agitating speed of 1,000 r.p.m. for 20 minutes. Then the content of the autoclave is heated to 70° C. within about 5 minutes, and the ethylene pressure is raised to 50 bar. Under a constant pressure of 50 bar and at an agitating speed of 1,000 r.p.m., the oligomerization is conducted for 165 minutes. The results are listed in Table 2.

TABLE 2

| Example No. | mmol NaBH₄ | Catalyst Activity (g. Olefins/ g. Ni . h) | Isomerization (% Butene-2 in Butene) | β | n-α-Olefin Content (%) |
| --- | --- | --- | --- | --- | --- |
| 9 | 5 | 315 | 1.0 | 3 | 99 |
| 10 | 7.5 | 130 | 1.2 | 2.5 | 98 |
| 11 | 10 | 350 | 1.0 | 3.5 | 100 |

The extent of isomerization and n-α-olefin content were determined as indicated in the preceding examples.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a nickel-containing catalyst for the oligomerization of ethylene wherein Ni is bonded to (a) a phosphine ligand, and also to (b) up to two other ligands which are a different phosphine, a phosphite, a phosphino alkylene, an arsine, a stibine, a bismuthine or an olefinically unsaturated compound of 2–20 carbon atoms, containing up to four olefinically unsaturated linkages and up to 3 carbocyclic rings the improvement wherein said ligand (a) is a secondary or tertiary 2-carboxyethyl- or carboxymethylphosphine or a salt thereof, of the formula
R—P(CH₂COOMe)₂   or   R—P(CH₂—CH₂—COOMe)₂ wherein Me is hydrogen, an alkali metal or NR'₄ wherein R' is hydrogen, $C_{1-10}$ alkyl or $C_{6-14}$ aryl, and R is hydrogen or a saturated or unsaturated, aliphatic or cycloaliphatic group of 1–20 carbon atoms and, for the 2-carboxyethylphosphines, also $C_{6-14}$ aryl.

2. A catalyst of claim 1, wherein R is a saturated or unsaturated, aliphatic cycloaliphatic group of 1–10 carbon atoms.

3. A catalyst of claim 1, wherein the phosphine ligand (a) is a 2-carboxyethylphosphine wherein Me is hydrogen, sodium or potassium and R is hydrogen, butyl, cyclohexyl or phenyl.

4. A catalyst of claim 1 wherein each of the other ligands (b) is a $C_{2-12}$ olefin of the formula

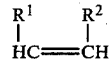

wherein R¹ and R² are alike or different and are hydrogen, or alkyl, cycloalkyl, akenyl, cycloalkenyl, aralkyl, aryl or alkaryl of up to 8 carbon atoms each, and wherein R¹ and R² together can also form a bivalent $C_{2-10}$ aliphatic group, having up to 3 additional olefinically unsaturated linkages as the only unsaturated C-C bonds.

* * * * *